(12) United States Patent
Ishikawa

(10) Patent No.: US 10,548,480 B2
(45) Date of Patent: Feb. 4, 2020

(54) OPTICAL COHERENCE TOMOGRAPHIC IMAGING BASED IMAGE PROCESSING APPARATUS AND IMAGE PROCESSING METHOD FOR IMAGING OBJECT AT A PLURALITY OF TIMES AT DIFFERENT FOCUS POSITIONS

(71) Applicant: SCREEN HOLDINGS CO., LTD., Kyoto (JP)

(72) Inventor: Naoki Ishikawa, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 15/692,406

(22) Filed: Aug. 31, 2017

(65) Prior Publication Data
US 2018/0055365 A1    Mar. 1, 2018

(30) Foreign Application Priority Data
Sep. 1, 2016   (JP) .................................. 2016-170507

(51) Int. Cl.
*A61B 5/00* (2006.01)
*G01B 9/02* (2006.01)
*G01N 21/25* (2006.01)

(52) U.S. Cl.
CPC ........ *A61B 5/0066* (2013.01); *G01B 9/02044* (2013.01); *G01B 9/02084* (2013.01); *G01B 9/02091* (2013.01); *G01N 21/25* (2013.01)

(58) Field of Classification Search
CPC ... G06T 7/55; G06T 5/50; G06T 2207/20216; G06T 2207/10101; G06T 2207/10148;
(Continued)

(56) References Cited

U.S. PATENT DOCUMENTS

| 8,425,037 B2 | 4/2013 | Uhlhorn et al. |
| 2009/0284748 A1* | 11/2009 | Melman ............... G01B 9/0201 356/479 |
| 2014/0016136 A1 | 1/2014 | Kawano et al. |

FOREIGN PATENT DOCUMENTS

| WO | 2008/139799 A1 | 11/2008 |
| WO | 2012/128367 A1 | 9/2012 |

OTHER PUBLICATIONS

P. Meemon et al., "Spectral fusing Gabor domain optical coherence microscopy," Optical Letters, 41(3): 508-511 (Feb. 1, 2016).
(Continued)

*Primary Examiner* — Hwa Andrew Lee
(74) *Attorney, Agent, or Firm* — McDermott Will & Emery LLP

(57) ABSTRACT

An image processing apparatus of the invention is for generating a tomographic image corresponding to a cross-section of an imaging object. The image processing apparatus 1 comprises: a data acquisitor 20 which obtains image data corresponding to a plurality of imaging with respect to the imaging object; and an image generator 30 which generates the tomographic image corresponding to the cross-section parallel to the depth direction based on the image data. The plurality of imaging are performed with mutually different focus positions in a depth direction and imaging ranges overlapped in the depth direction. The image generator 30 sets a value of each pixel in the tomographic image at a value obtained by a calculation process between the image data of a same position of the imaging object corresponding to the pixel obtained at each of the plurality of imaging.

8 Claims, 11 Drawing Sheets

(58) Field of Classification Search
CPC .......... G06T 2207/20221; G01N 21/25; G01L 39/02044; G01B 9/02084; G01B 9/02091; G01B 9/02044; A61B 5/0066
See application file for complete search history.

(56) References Cited

OTHER PUBLICATIONS

J. P. Rolland et al., "Gabor Domain Optical Coherence Microscopy," Optical Coherence Tomography and Coherence Techniques IV, vol. 7372 of Proceedings of SPIE-OSA Biomedical Optics, paper 7372_1K, pp. 1-7 (Jul. 14, 2009).
P. Meemon et al., "Sub-cellular resolution imaging with Gabor domain optical coherence microscopy," Optical Coherence Tomography and Coherence Domain Optical Methods in Biomedicine XIV, vol. 7554 of the Proceedings of SPIE, paper 75542C, pp. 1-9 (Feb. 20, 2010).
Extended European Search Report issued in corresponding EP Patent Application No. 17187262.5, dated Nov. 28, 2017.

* cited by examiner

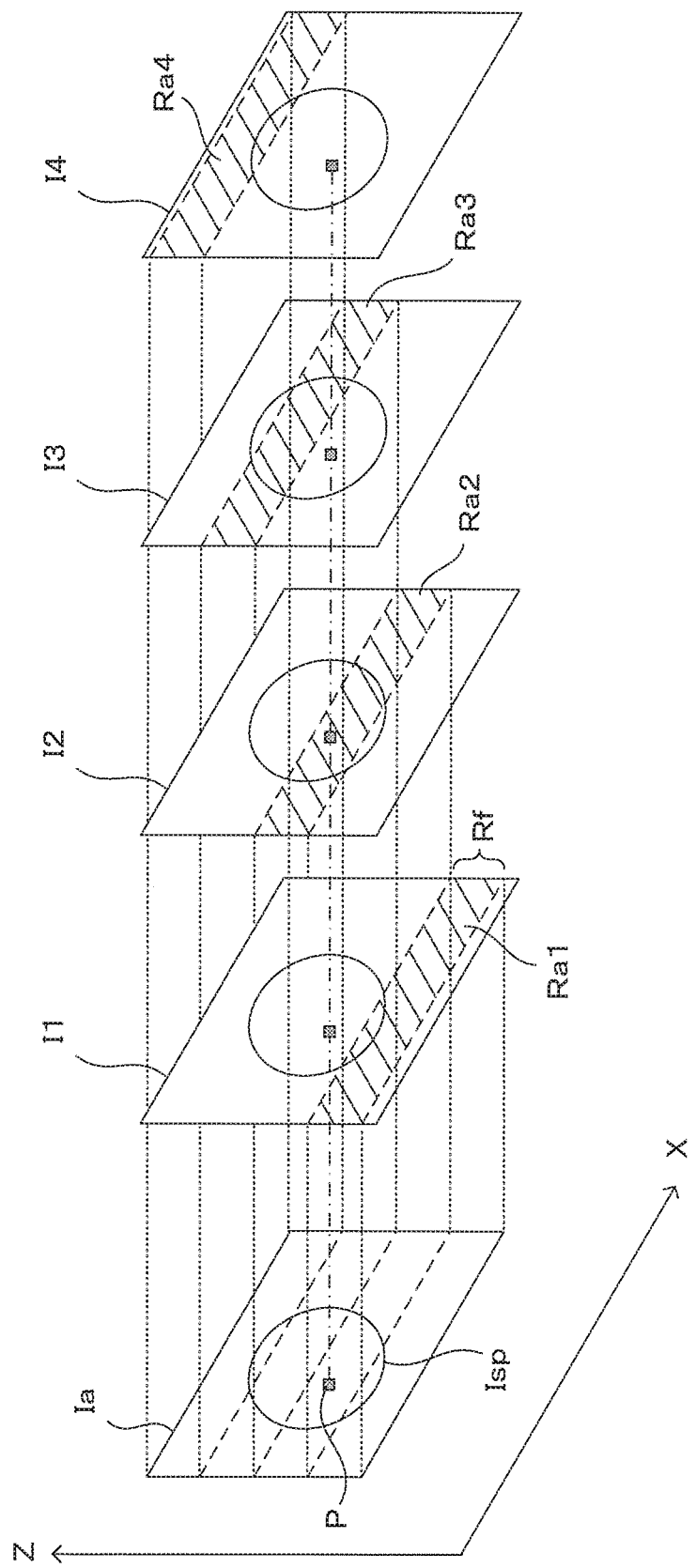
F I G. 6

OPTICAL COHERENCE TOMOGRAPHIC IMAGING BASED IMAGE PROCESSING APPARATUS AND IMAGE PROCESSING METHOD FOR IMAGING OBJECT AT A PLURALITY OF TIMES AT DIFFERENT FOCUS POSITIONS

CROSS REFERENCE TO RELATED APPLICATION

The disclosure of Japanese Patent Application No.2016-170507 filed on Sep. 1, 2016 including specification, drawings and claims is incorporated herein by reference in its entirety.

BACKGROUND OF THE INVENTION

1. Field of the Invention

This invention relates to a technique for generating a tomographic image of an imaging object using an optical coherence tomography technique.

2. Description of the Related Art

In technical fields of medicine and biochemistry, samples carried in an appropriate carrier such as cells and microorganisms cultured in a container are observed. Techniques for imaging cells and the like using a microscope or the like are proposed as methods for observation without affecting the cells and the like to be observed. One of such techniques utilizes an optical coherence tomography technique. In this technique, low-coherence light emitted from a light source is caused to be incident as illumination light on an imaging object and interference light of reflected light (signal light) from the imaging object and reference light having a known optical path length is detected, whereby an intensity distribution in a depth direction of the reflected light from the imaging object is obtained for tomographic imaging.

For a higher image resolution, it is thought to increase an NA (Numerical Aperture) of illumination light to be incident on an imaging object. By doing so, a resolution in a horizontal direction perpendicular to an incident direction of the illumination light can be improved. However, in an optical system having a large NA, a focusing range in a depth direction becomes narrower since a depth of focus (or depth of field) of the optical system becomes shallower. Thus, in the depth direction, a range capable of imaging with good image quality becomes narrow. In such a case, a tomographic image of the entire imaging object may be generated by splicing a plurality of partial images obtained at different focus positions in the depth direction.

For example, a technique for generating one tomographic image by splicing a plurality of focused images having a narrow observation range in a depth direction is described in the specification of International Publication No. 2012/128367. In this technique, to accurately align a plurality of focused images and synthesize an image, each focused image is arranged at a position having a highest correlation with an image in a wide range obtained using an optical system having a small NA.

In an optical tomographic imaging technique for performing imaging using coherence light as illumination light, random spot-like noise due to the interference of light reflected by fine unevenness of an imaging object is known to appear in an image. For example, if an imaging object is a cell or a cell cluster, the imaging object behaves as a semitransparent and irregular multi-layered scatterer. Thus, noise due to the interference of reflected light from each layer increases. Such a noise is called speckle noise.

Although the above conventional technique can obtain a tomographic image having a high resolution and a wide observation range, the influence of such speckle noise is not considered. Thus, there remains a room for improvement in terms of the quality of a tomographic image to be generated.

SUMMARY OF THE INVENTION

This invention was developed in view of the above problem and an object thereof is to provide a technique capable of simultaneously realizing a reduction of speckle noise in splicing tomographic images imaged at a plurality of different times in a technique for generating a tomographic image of an imaging object using an optical tomographic imaging technique.

To achieve the above object, one aspect of this invention is directed to an image processing apparatus for generating a tomographic image corresponding to a cross-section of an imaging object. The image processing apparatus comprises: a data acquisitor which obtains image data corresponding to a plurality of imaging with respect to the imaging object by optical coherence tomographic imaging; and an image generator which generates the tomographic image corresponding to the cross-section parallel to the depth direction based on the image data, wherein: the plurality of imaging are performed with mutually different focus positions in a depth direction along an incident direction of illumination light and imaging ranges overlapped in the depth direction; and the image generator sets a value of each pixel in the tomographic image at a value obtained by a calculation process between the image data of a same position of the imaging object corresponding to the pixel obtained at each of the plurality of imaging.

Further, to achieve the above object, another aspect of this invention is directed to an image processing method for generating a tomographic image corresponding to a cross-section of an imaging object. The image processing method comprises: a data acquisition to obtain image data corresponding to imaging performed a plurality of times with respect to the imaging object by optical coherence tomographic imaging; and an image generation to generate the tomographic image corresponding to the cross-section parallel to the depth direction based on the image data, wherein: the plurality of imaging are performed with mutually different focus positions in a depth direction along an incident direction of illumination light and imaging ranges overlapped in the depth direction; and a value of each pixel of the tomographic image is set at a value obtained by a calculation process between the image data of a same position of the imaging object corresponding to the pixel obtained at each of the plurality of imaging.

Speckle noise is generated by the interference of each reflected light from a plurality of positions of an imaging object. Thus, the speckle noise is random noise on the surface, but is reproducible if an incidence condition when illumination light is incident on the imaging object and a light receiving condition when the reflected light from the imaging object is received are the same. Conversely speaking, how noise appears differs if at least one of these conditions is changed.

Accordingly, in the invention, the same imaging range of the imaging object is imaged at different focus positions a plurality of times. This makes speckle noise appearing positions uncorrelated with each other in imaging a plurality of times. Thus, the influence of the speckle noise can be reduced by calculation between image data representing contents of images at the same position obtained by imaging at different times. Further, even if the entire imaging object cannot be located in the focusing range by imaging one time, a tomographic image can be generated by splicing parts with good image quality obtained by imaging each time by determining the value of the pixel at each position in the tomographic image based on the image data obtained by imaging at different focus positions at a plurality of times.

As described above, according to the invention, the value of the pixel at each position is obtained by calculation between the image data obtained by imaging a plurality of times corresponding to this position to splice tomographic images imaged at different focus positions in the technique for generating a tomographic image of an imaging object using an optical tomographic imaging technique. By doing so, speckle noise can also be reduced.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 6 is a diagram showing a concept of generating one tomographic image by synthesizing a plurality of raw images.

DETAILED DESCRIPTION OF THE PREFERRED EMBODIMENTS

Figure 1:
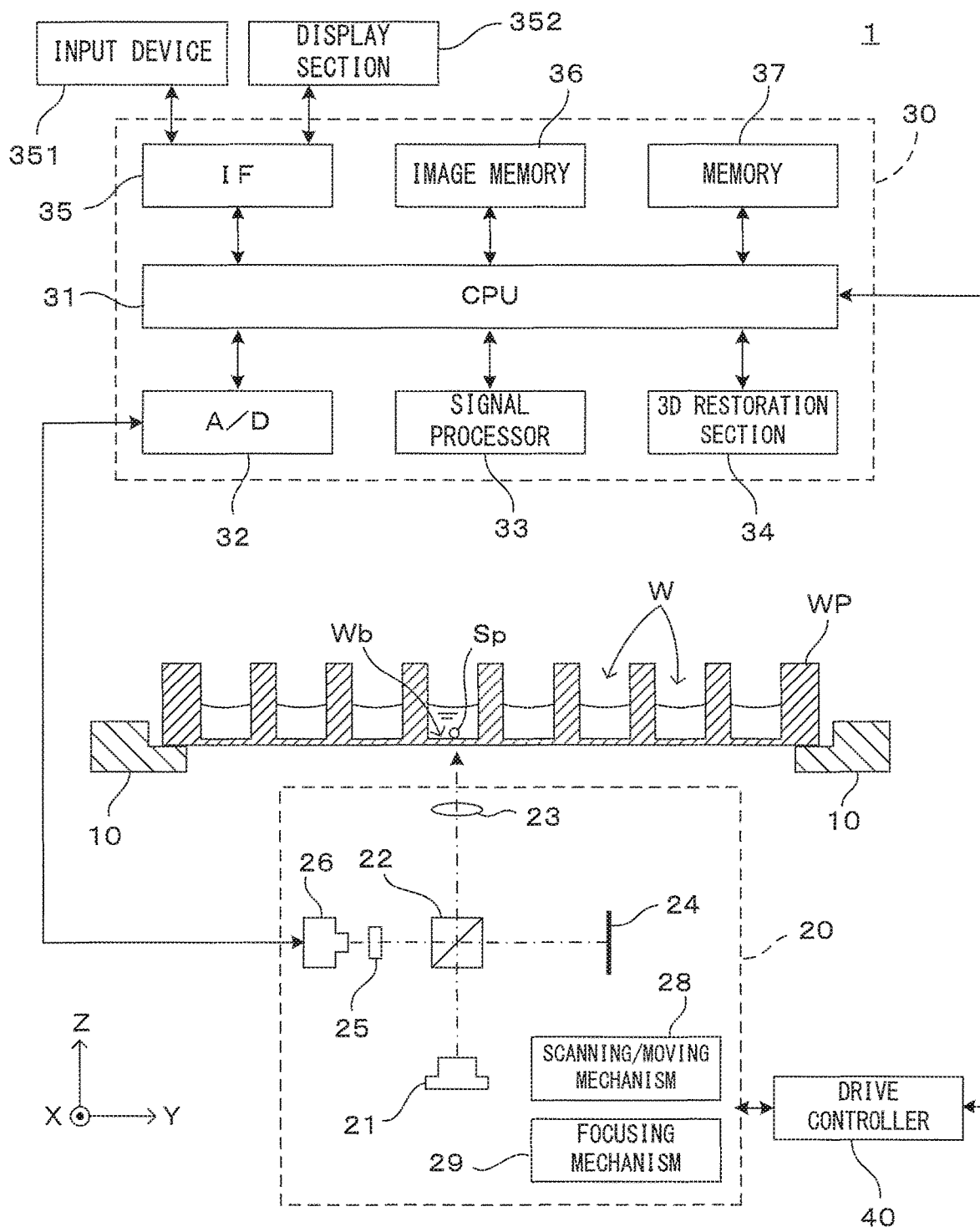
FIG. 1 is a drawing which shows an embodiment of the imaging apparatus according to the invention.

FIG. 1 is a drawing which shows an embodiment of the imaging apparatus according to the invention. The image processing apparatus 1 tomographically images a spheroid (cell aggregate) cultured in liquid (culture liquid, for example), processes the obtained tomographic image and generates a stereoscopic image of the spheroid. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The image processing apparatus 1 comprises a holder 10. The holder 10 holds in an approximately horizontal posture a well plate (which is also called a "micro-plate") WP, in which a number of dents (wells) W which can hold a liquid at the top surface of a plate-like member, in such a manner that the openings of the wells W are directed toward above. A predetermined amount of an appropriate culture liquid is poured in each well W of the well plate WP in advance, and a spheroid Sp is cultured in the liquid at the bottom surface Wb of the well W. Although FIG. 1 shows the spheroids Sp only in some wells W, the spheroid Sp is cultured in each one of the wells W.

An imaging unit 20 is disposed below the well plate WP which is held by the holder 10. The imaging unit 20 is an optical coherence tomography (OCT) apparatus capable of imaging tomographic images of a target object (imaging object) in a non-contact non-destructive (non-invasive) manner. The imaging unit 20 which is an OCT apparatus comprises a light source 21 which emits illumination light for the imaging object, a beam splitter 22 which splits light from the light source 21, an objective lens 23, a reference mirror 24, a spectroscope 25 and a photo-detector 26.

Further, the image processing apparatus 1 comprises a control unit 30 which controls operations of the apparatus and a drive controller 40 which controls movement of movable parts of the imaging unit 20. The control unit 30 comprises a CPU (Central Processing Unit) 31, an A/D convertor 32, a signal processor 33, a 3D restoration section 34, an interface (IF) section 35, an image memory 36 and a memory 37.

The CPU 31 governs operations of the entire apparatus by executing a predetermined control program. The control program executed by the CPU 31 and data which are generated during processing are saved in the memory 37. The A/D convertor 32 converts a signal which the photo-detector 26 of the imaging unit 20 outputs in accordance with the amount of received light into digital image data. The signal processor 33 performs image processing described later based upon a digital data outputted from the A/D converter 32, thereby generates a tomographic image of the imaging object. Based upon image data of a plurality of tomographic images, the 3D restoration section 34 generates a stereoscopic image (3D image) of the imaged cell aggregate. The image memory 36 saves the image data of the tomographic images generated by the signal processor 33 and the image data of the stereoscopic image generated by the 3D restoration section 34.

The interface section 35 realizes communication between the image processing apparatus 1 and outside. More specifically, the interface section 35 has a function of communicating with external equipment, and a user interface function of accepting manipulation by a user and informing the user of various types of information. For this purpose, an input device 351 and a display section 352 are connected to the interface section 35. The input device 351 is for instance a key board, a mouse, a touch panel or the like which can accept manipulation and entry concerning selection of the functions of the apparatus, setting of operating conditions, etc. The display section 352 comprises a liquid crystal display for example which shows various types of processing results such as the tomographic images imaged by the imaging unit 20 and the stereoscopic image generated by the 3D restoration section 34.

Further, the drive controller 40 makes the imaging unit 20 scan and move in accordance with a control command given from the CPU 31. The movable mechanism of the imaging unit 20 includes a scanning/moving mechanism 28 for integrally moving the entire imaging unit 20 in a Y direction and a focusing mechanism 29 for adjusting a focus position of an objective lens 23 in a Z-direction by moving the objective lens 23 in the Z direction. As described next, the tomographic images of the cell aggregate which is the imaging object are obtained owing to combination of scan moving of the imaging unit 20 executed by the drive controller 40 and detection of the amount of the received light by the photo-detector 26.

Figure 2A:
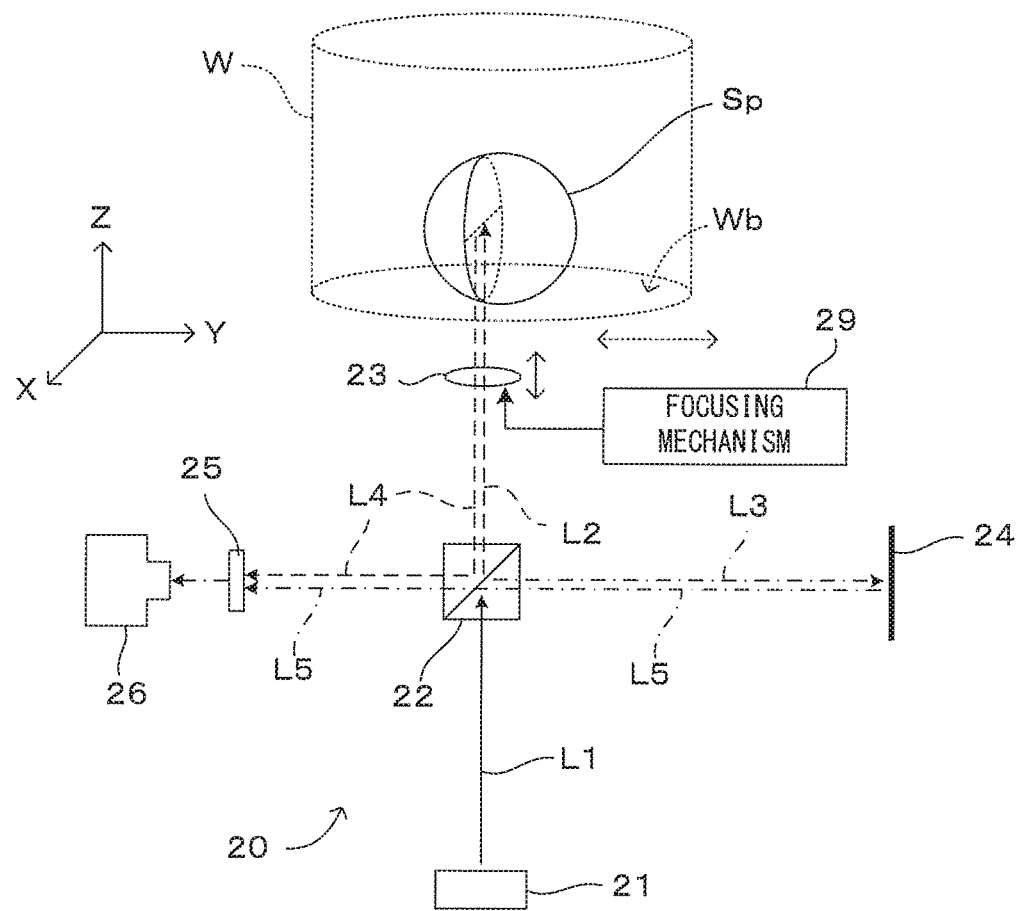
FIGS. 2A and 2B are drawings for describing the principle of imaging in this image processing apparatus.
Figure 2B:
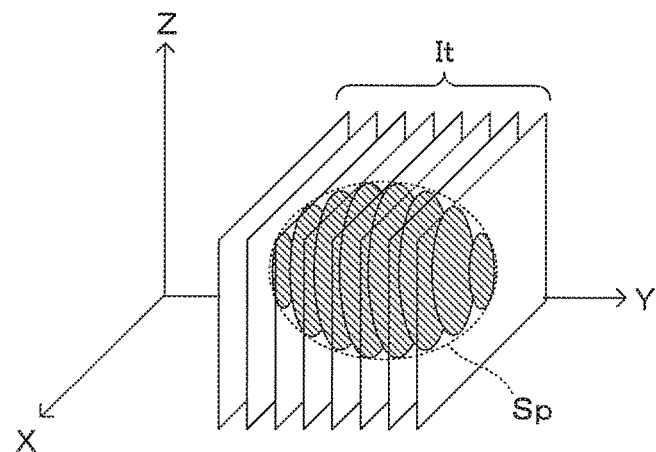

FIGS. 2A and 2B are drawings for describing the principle of imaging in this image processing apparatus. More specifically, FIG. 2A is a drawing which shows optical paths inside the imaging unit 20, and FIG. 2B is a schematic drawing which shows tomographic imaging of a spheroid. As described earlier, the imaging unit 20 works as an optical coherence tomography (OCT) apparatus.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22, and some light L2 indicated by the broken-line arrow propagates toward the well W, and some light L3 indicated by the arrow of long dashed short dashed line propagates toward the reference mirror 24.

The light L2 propagating toward the well W is incident on the well W by way of the objective lens 23. More specifically, the light L2 emitted from the beam splitter 22 is incident on the well bottom surface Wb via the objective lens 23. The objective lens 23 has a function of converging the light L2 propagating from the beam splitter 22 toward the well W to the imaging object in the well W (spheroid Sp in this case) and a function of collecting the reflected light emitted from the imaging object and causing it to propagate toward the beam splitter 22.

The objective lens 23 is movable in the Z direction by the focusing mechanism 29. This enables the focus position of the objective lens 23 with respect to the imaging object to be changed in the Z direction. An optical axis of the objective lens 23 is parallel to a vertical direction and, therefore, perpendicular to the well bottom surface Wb in the form of a flat surface. Further, an incident direction of illumination light on the objective lens 23 is parallel to the optical axis, and the arrangement of the objective lens 23 is determined such that a light center of the light coincides with the optical axis. Instead of the single objective lens 23, an optical system including a plurality of optical elements may be used.

The light L2 is reflected at the surface of the spheroid Sp unless the spheroid Sp transmits the light beam L2. On the other hand, when the spheroid Sp has a property of transmitting the light beam L2 to a certain extent, the light beam L2 propagates into inside the spheroid Sp and is reflected by a structure element which is inside the spheroid. When the near infrared rays for instance are used as the light beam L2, it is possible to allow the incident light to reach even inside the spheroid Sp. The reflected light from the spheroid Sp is irradiated as scattered light in various directions. Out of that, light L4 irradiated within a light collection range of the objective lens 27 is collected by the objective lens 23 and sent to the beam splitter 22.

The reflected light L4 reflected by a surface or an internal reflecting surface of the spheroid Sp and reference light L5 reflected by the reference mirror 24 are incident on the photo-detector 26 via the beam splitter 22. At this time, interference due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component by the spectroscope 25 and received by the photo-detector 26.

By Fourier transforming the interference signal output from the photo-detector 26 according to the interference light detected by the photo-detector 26, the reflected light intensity distribution in the depth direction, i.e. in the Z direction at an incident position of the light beam L2 on the spheroid Sp is obtained. By scanning the light beam L2 incident on the well W in the X direction, a reflected light intensity distribution in a plane parallel to an XZ plane can be obtained and a tomographic image of the spheroid Sp having a cross-section on this plane can be generated from that result. In this description, "imaging one time" means an operation in which one tomographic image It of a cross section parallel to a XZ plane is obtained by scanning beam in X direction.

As indicated by the dotted-line arrow, the relative position of the imaging unit 20 to the well W is changed along the Y direction over multiple steps, and a tomographic image is imaged for every change. As a result, as shown in FIG. 2B, a number of tomographic images It of the spheroid Sp are obtained along cross-sectional surfaces which are parallel to the XZ plane. As the scan pitch in the Y direction is reduced, it is possible to obtain image data with sufficient resolution to grasp the stereoscopic structure of the spheroid Sp. Scan movements of the respective parts above in the imaging unit 20 are realized as the drive controller 40 makes the scanning/ moving mechanism 28 operate after receiving a control command from the CPU 31.

Note that the imaging unit 20 causes the interference of the reflected light from the imaging object and the reference light from the reference mirror 24 using the beam splitter 22 in the above. However, besides this, there is also an OCT apparatus for causing the interference of reflected light and reference light using an optical fiber coupler. As described later, the OCT apparatus of such a type can be applied also in this embodiment.

Next, an imaging operation of a tomographic image by this image processing apparatus 1 is described in more detail. As described above, in the FD-OCT imaging apparatus, a reference light intensity distribution in a depth direction (Z direction) along an incident direction of illumination light can be obtained by the Fourier transform of a spectrum of interference light. By changing an incident position of the light in an X direction by scanning the illumination light, a reference light intensity distribution at positions different in the horizontal direction (X direction) can be obtained. From these pieces of information, a tomographic image of an imaging object having a cross-section parallel to an XZ plane is obtained.

Here, a method for further improving the quality of a tomographic image is studied. First, for the horizontal direction (X direction), it is thought to increase a numerical aperture (NA) of the optical system such as the objective lens 23 in order to increase a resolution in this direction. However, as described next, there is a problem of narrowing a range in which good image quality is obtained in the depth direction (Z direction) if the NA of the optical system is increased.

Figure 3A:
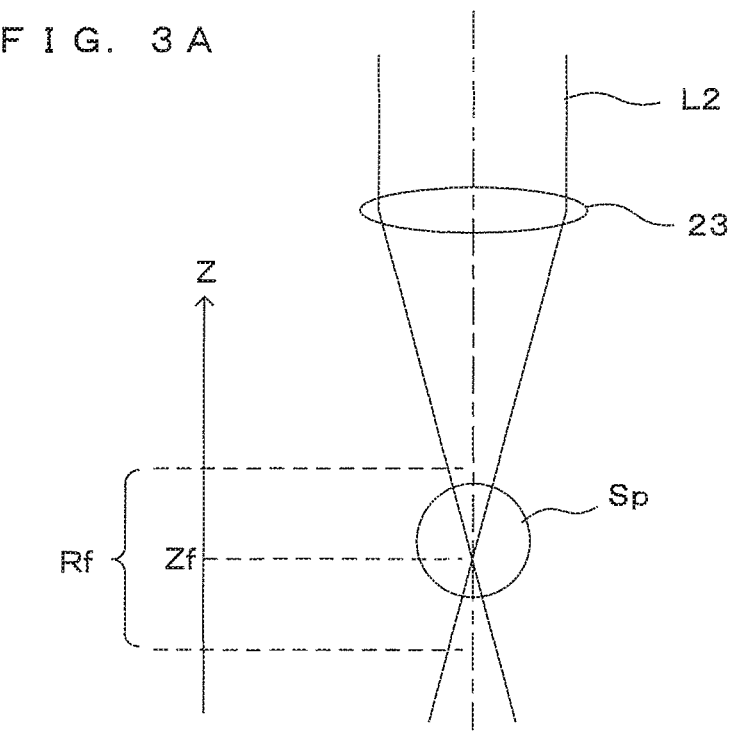
FIGS. 3A and 3B are diagrams showing a state of imaging using an optical system having a relatively small NA.
Figure 3B:
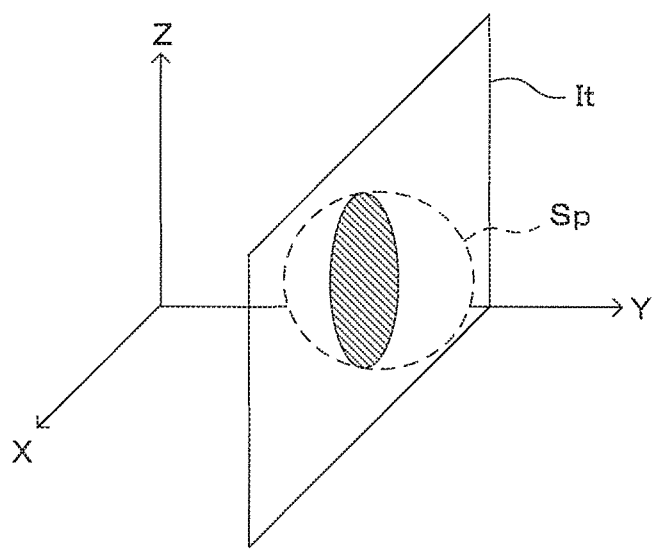
Figure 4A:
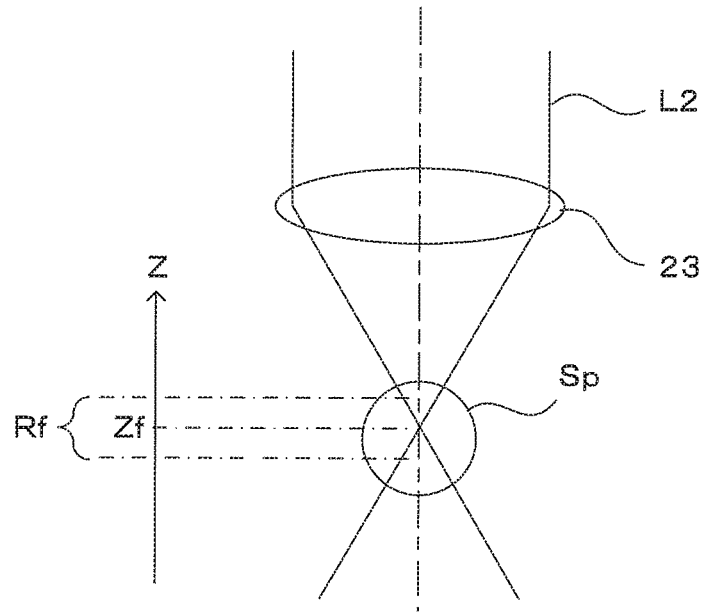
FIGS. 4A and 4B are diagrams showing a state of imaging using an optical system having a relatively large NA.
Figure 4B:
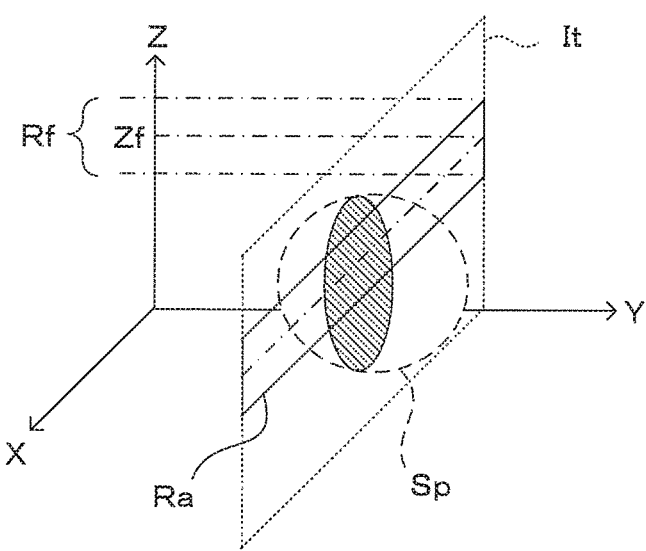

FIGS. 3A and 3B are diagrams showing a state of imaging using an optical system having a relatively small NA. FIGS. 4A and 4B are diagrams showing a state of imaging using an optical system having a relatively large NA. More specifically, FIG. 3A is a diagram showing a focusing range in the case of using an objective lens 23 having a relatively small NA and FIG. 3B is a diagram showing an example of a tomographic image obtained in the case of using such an objective lens 23. On the other hand, FIG. 4A is a diagram showing a focusing range in the case of using an objective lens 23 having a relatively large NA and FIG. 4B is a diagram showing an example of a tomographic image obtained in the case of using such an objective lens 23.

As shown in FIG. 3A, a relatively deep depth of field is obtained in the case of using the objective lens 23 having a relatively small NA. Thus, in the depth direction (Z direction), a range (focusing range) Rf regarded as a focused state with the focus position Zf as a center is relatively wide. For example, as shown in FIG. 3B, the entire spheroid Sp, which is an imaging object, is located in the focusing range in the depth direction and a tomographic image It of the spheroid Sp in one cross-section parallel to the XZ plane is obtained by imaging one time.

On the other hand, since a depth of field becomes shallower in the case of using the objective lens 23 having a relatively large NA as shown in FIG. 4A, the focusing range Rf in the depth direction becomes narrower than in the above case. Thus, as shown by solid line in FIG. 4B, out of a tomographic image It obtained by imaging one time, a range imaged in a focused state and expected to have good image quality, i.e. a range of a region Ra included in the depth of field with the focus position Zf as a center in the depth direction, is more limited. Therefore, to obtain a tomographic image having good image quality for one entire cross-section of the spheroid Sp, it is necessary to perform imaging a plurality of times with the focusing range Rf made different in the Z direction and extract and synthesize regions having good image quality from the respective images.

Note that, in OCT imaging, the position of the imaging object in the depth direction is specified as a distance from a reference plane determined by an optical path length of reference light L5. Thus, if the optical path length of the reference light L5 remains unchanged, the focusing range Rf only moves in the Z direction in the tomographic image It even if the focus position Zf of the objective lens 23 changes in the Z direction. Specifically, an imaging range in which the tomographic image It obtained by imaging each time covers the imaging object is substantially the same.

In this embodiment, the focus position of the objective lens 23 can be changed in the Z direction by the focusing mechanism 29. By performing imaging a plurality of times at different focus positions of the objective lens 23 in the Z direction, a plurality of tomographic images at mutually different focusing positions Zf in the Z direction can be obtained. By partially extracting these tomographic images and splicing the extracted images, a tomographic image for one cross-section parallel to the XZ plane can be generated. A process for this is described below.

Figure 5:
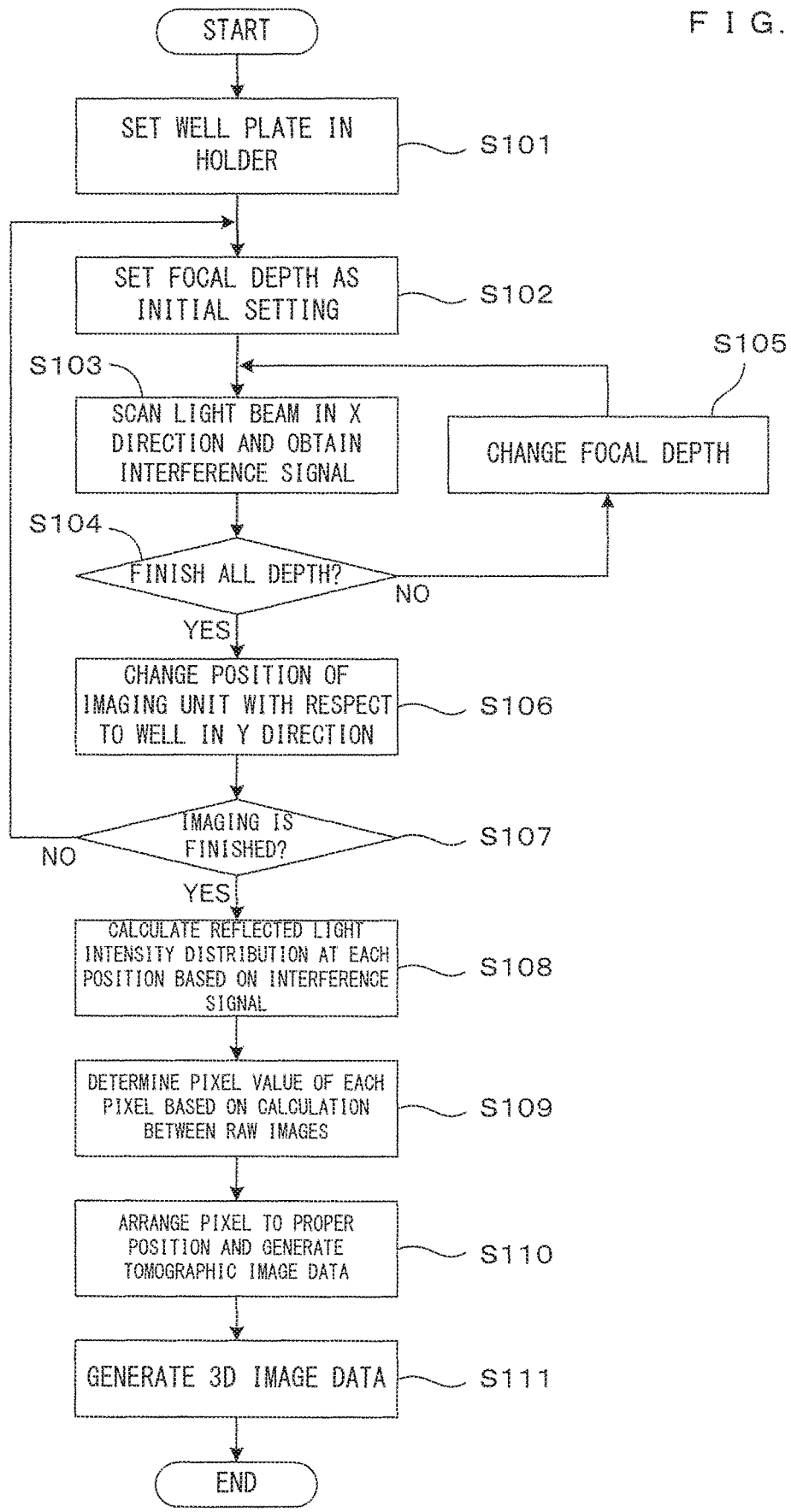
FIG. 5 is a flow chart showing the operation of this image processing apparatus.

FIG. 5 is a flow chart showing the operation of this image processing apparatus. This operation is realized by the CPU 31 implementing a control program written in the memory 37 in advance to control each unit of the apparatus and cause each unit to perform a predetermined operation. The well plate WP carrying spheroids SP to be imaged together with a culture liquid is set in the holder 10 by a user or a conveyor robot (Step S101). The CPU 31 controls the imaging unit 20 and the drive controller 40 to tomographically image the spheroid Sp in the well W, which is an imaging object.

More specifically, the focus position (focal depth) of the objective lens 23 in the depth direction is set at an initial position determined in advance by the focusing mechanism 29 (Step S102). In this state, an incident position on the well W is changed in the X direction by scanning a light beam L2, interference light at each position is detected by the photodetector 26 and an interference signal in a cross-section parallel to the XZ plane is obtained (Step S103). This operation corresponds to imaging one time. The interference signal is converted into digital data and stored and saved in the memory 37.

Until imaging is finished for all focal depths determined in advance (Step S104), the focal depth of the objective lens 23 is changed and set by the focusing mechanism 29 (Step S105) and imaging in Step S103 is performed every time. A change amount of the focal depth in each step is described later. The data of the interference signal obtained by imaging one time includes detailed information on the focusing range of a part of the tomographic image. Data obtained by imaging performed at a plurality of times with different focusing ranges represents one tomographic image as a whole.

The process of Steps S102 to S105 described above is repeated until imaging for the entire well W is finished (Step S107) while a relative position of the imaging unit 20 with respect to the well W is changed at a predetermined interval in the Y direction by the scanning/moving mechanism 28 (Step S106). In this way, interference signals corresponding to a plurality of tomographic images at different focus positions are obtained.

The signal processor 33 calculates a reflected light intensity distribution in the depth direction at each position based on the interference signal obtained at each position of the well W in this way (Step S108). Specifically, the reflected light intensity distribution is obtained by the Fourier transform of a spectrum distribution of the interference light obtained from the interference signal. Tomographic image data representing one tomographic image is generated from the thus obtained reflected light intensity distribution. This calculation is individually performed for the individual tomographic image obtained by imaging at each of a plurality of times. The thus obtained tomographic images are images imaged only partly in the focused state and serve as raw materials for a final tomographic image to be generated by synthesis. For distinction from the final tomographic image, the individual tomographic image obtained by imaging each time is referred to as a "raw image" and tomographic image data representing the raw image is referred to as "raw image data" below.

Next, the signal processor 33 synthesizes a plurality of raw images to generate a tomographic image comprehensively representing one cross-section of the imaging object (Steps S109, S110). Specifically, a pixel value of each pixel constituting the final tomographic image is determined by calculation between pieces of the raw image data corresponding to the position of this pixel in each of the plurality of raw images obtained by imaging each time (Step S109). A calculation method is described later. By arranging the pixels having the pixel values determined in this way at corresponding positions on an image plane, tomographic image data corresponding to the tomographic image synthesized from the plurality of raw images is obtained (Step S110). Tomographic image data is similarly generated at each position in the Y direction and the generated tomographic image data is stored and saved in the image memory 36.

Based on the thus obtained tomographic image data, the 3D restoration section 34 generates 3D image data corresponding to a stereoscopic image of the spheroid Sp (Step S111). Specifically, the 3D image data can be obtained, for example, by interpolating the tomographic image data, which is discretely obtained in the Y direction, in the Y direction. A technique for generating 3D image data from tomographic image data is not described in detail since it is already in practical use.

FIG. 6 is a diagram showing a concept of generating one tomographic image by synthesizing a plurality of raw images. As shown in FIG. 6, one tomographic image Ia entirely containing an image Isp corresponding to a spheroid, which is an imaging object, is obtained by synthesizing a plurality of tomographic images (raw images) obtained by imaging each time. Here, it is assumed that the tomographic image Ia is generated from four raw images I1 to I4 obtained by imaging four times.

In the individual raw images I1 to I4, the positions of hatched regions (focusing regions) Ra1 to Ra4 in the focusing range Rf are different from each other in the Z direction due to differences in the focus position. However, as described above, imaging ranges in the depth direction are equal to each other and the positions of the spheroid images Isp occupying in the respective raw images are substantially the same if the optical path length of the reference light L5 is the same. However, regions included in the focusing range of the objective lens 23 and expected to have good image quality are only partial regions and those are the focusing regions Ra1 to Ra4.

To improve the image quality of the tomographic image Ia to be synthesized, only the focusing regions Ra1 to Ra4 are preferably extracted from the respective raw images I1 to I4 and spliced. A point P corresponding to an arbitrary pixel constituting the tomographic image Ia is present in each of the raw images I1 to I4. For the above purpose, however, the arbitrary point P is desirably in the focusing region of at least one raw image. In an example of FIG. 6, the point P is located in the focusing region Ra2 of the raw image I2.

Figure 7A:
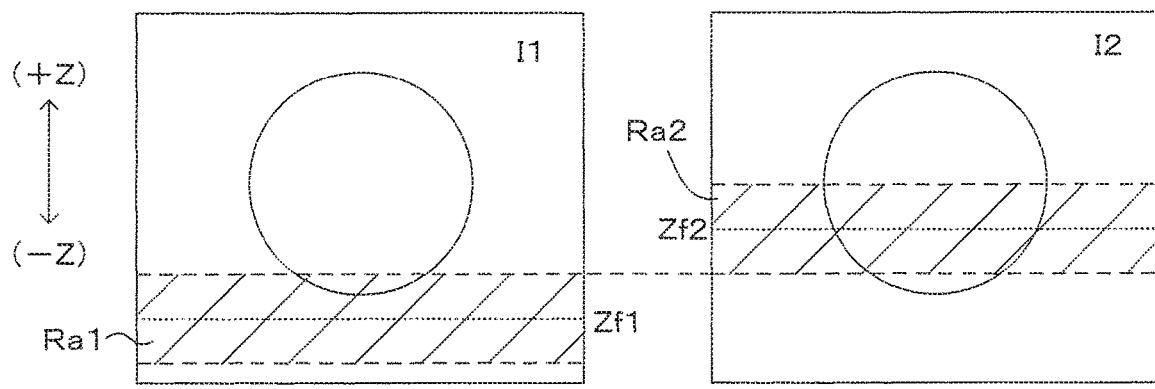
FIGS. 7A to 7C are diagrams showing the position of the focusing region in each raw image.
Figure 7B:
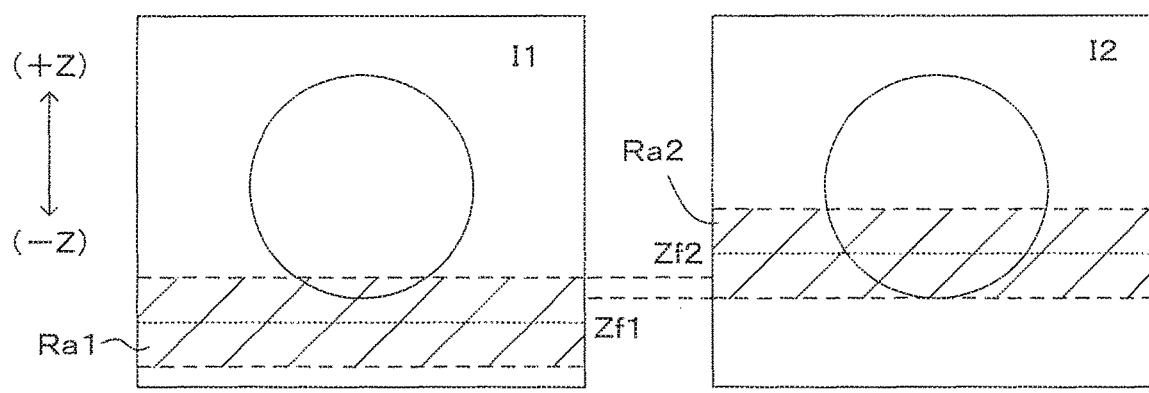
Figure 7C:
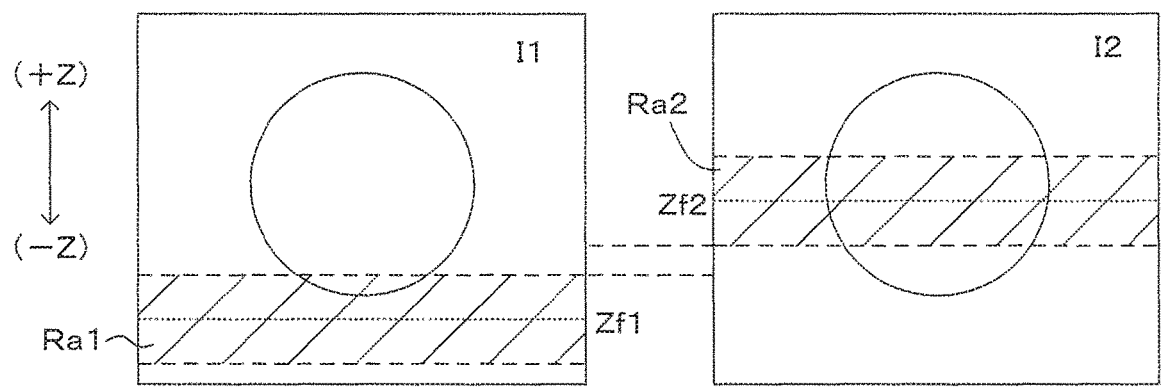

FIGS. 7A to 7C are diagrams showing the position of the focusing region in each raw image. Here, the overlap between one raw image I1 and another raw image I2 having a focus position during imaging closest to that of the raw image I1 is thought. In the figures, Zf1, Zf2 denote the focus positions of the raw images I1, I2 in the depth direction respectively. By appropriately setting a change amount of the focal depth for imaging each time, various positional relationships as shown in FIGS. 7A to 7C can be realized.

In an example shown in FIG. 7A, an end position of the focusing region Ra1 of the raw image I1 on a (+Z) side is substantially the same as an end position of the focusing region Ra2 of the raw image I2 on a (−Z) side. In such a relationship, a synthesized image entirely in the focused state can be generated by extracting and splicing the entire respective focusing regions Ra1, Ra2. According to such an imaging method, the synthesized image can be generated, effectively utilizing the entireties of the focusing regions Ra1, Ta2 of the respective raw images I1, I2.

On the other hand, in an example shown in FIG. 7B, the end position of the focusing region Ra1 of the raw image I1 on the (+Z) side is closer to the (+Z) side than the end position of the focusing region Ra2 of the raw image I2 on the (−Z) side. Thus, the focusing regions Ra1, Ra2 partially overlap each other. Also by such an imaging method, a synthesized image entirely in the focused state can be generated. However, since the focusing regions overlap and more imaging is necessary than in the case of FIG. 7A to obtain a synthesized image covering the same area range, it takes a longer time for imaging.

In contrast, in an example shown in FIG. 7C, the end position of the focusing region Ra1 of the raw image I1 on the (+Z) side is closer to the (−Z) side than the end position of the focusing region Ra2 of the raw image I2 on the (−Z) side. That is, there is a gap in the Z direction between the respective focusing regions Ra1 and Ra2. In such an imaging method, a synthesized image cannot be entirely in the focused state unless there is another raw image including this gap part in the focusing region. However, image quality is reduced with distance from the focus position, but an extreme image change is not necessarily found on the end parts of the focusing regions Ra1, Ra2. Thus, certain image quality can be maintained if the gap is small. At this time, the number of raw images necessary to obtain a synthesized image may be smallest and a processing time can be shortened by reducing the number of times of imaging.

As just described, the magnitude of the overlap of the focusing regions of a plurality of raw images, in other words, the change amount of the focal depth during imaging can be appropriately set depending on the purpose such as required image quality and a length of the processing time. Unless otherwise specified, it is assumed below that imaging is performed in the case shown in FIG. 7A where image quality and a small number of times of imaging are balanced. Of course, the following description is similarly applicable also for cases where the imaging methods shown in FIGS. 7B and 7C are applied.

As described above, the tomographic image Ia covering the entire imaging object is generated by partially extracting the plurality of raw images I1 to I4 imaged at different focal depths and synthesizing the extracted parts. Most simply, it is thought to extract and synthesize the focusing regions Ra1 to Ra4 of the respective raw images. However, in the OCT imaging technique using coherence light as illumination light, random noise called speckle noise may appear in an image.

Particularly when cells, spheroids or the like in a culture liquid are an imaging object, these cells or the like are regarded as an irregular multi-layered scatterer. Thus, many speckles of noise appear also in the focusing regions Ra1 to Ra4. Therefore, it is not possible to deal with image quality degradation due to speckle noise merely by extracting the focusing regions Ra1 to Ra4 from the raw images and splicing the focusing regions Ra1 to Ra4.

To deal with this problem, by calculating raw image data corresponding to the same position between a plurality of raw images, a pixel value of a pixel occupying this position in the synthesized tomographic image Ia is determined in this embodiment. How speckle noise appears differs in each image due to a difference in focal depth. Utilizing this, the influence of speckle noise in the tomographic image Ia after synthesis can be reduced by appropriate calculation between pieces of the raw image data.

Figure 8:
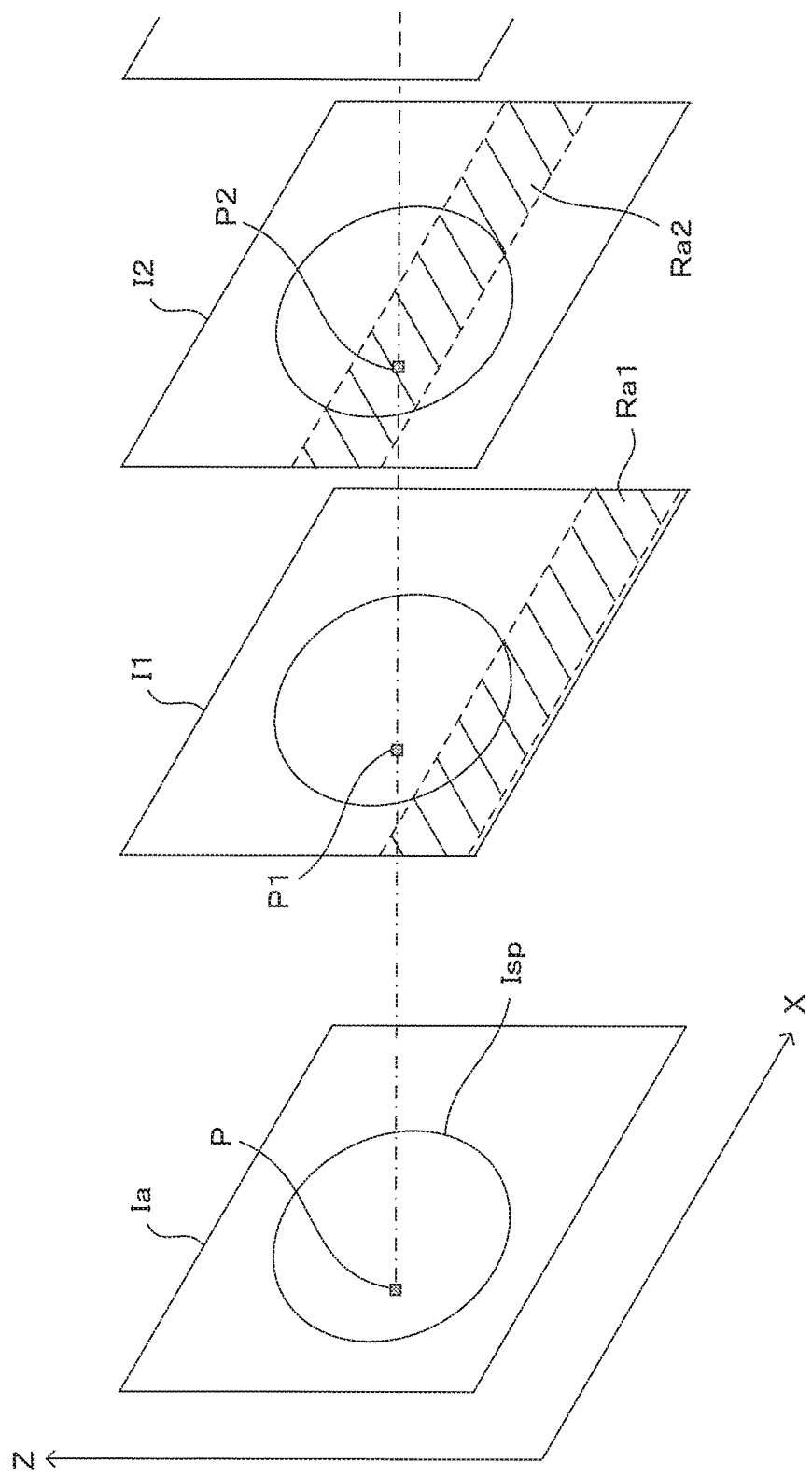
FIG. 8 is a diagram showing a process of reducing speckle noise.

FIG. 8 is a diagram showing a process of reducing speckle noise. Although calculation between two raw images I1 and I2 is described here, the same way of thinking applies also for a process between other raw images or a process among three or more raw images. Further, although a process for the point (pixel) P belonging to the inside of the image Isp of the spheroid is described here, a similar process is possible also for a background part outside the spheroid. Note that it is assumed below that "image information at a certain point (or pixel)" means information representing a density at a position in an image corresponding to this point (or pixel).

A point P2 in the raw image I2 corresponding to the point P is in the focusing region Ra2, but a corresponding point P1 in the raw image I1 at the different focus position during image is slightly deviated from the focusing region Ra1. In the case of not considering the influence of speckle noise, the pixel value of the corresponding point P is determined using only the image information of the point P2 located in the focusing region and more clearly imaged. However, the image information of the point P2 may possibly include speckle noise.

On the other hand, the influence of speckle noise appearing in the image information of the point P1 in the raw image I1 corresponding the point P is not directly correlated with speckle noise appearing in the image information of the point P2. Thus, if the pixel value of the point P is determined by appropriate calculation between the raw image data of the point P1 and that of the point P2, the influence of speckle noise appearing in the pixel value of the point P can be reduced.

If the point P is deviated from the focusing region Ra1, the contrast and clearness of the image are somewhat reduced. However, visually confirmed image quality is largely improved by reducing the influence of speckle noise. Unless the point P1 is largely distant from the focusing region Ra1 of the raw image I1, image quality is a little degraded. Further, if the focusing regions overlap between two raw images as shown in FIG. 7B and the point P1 is included in the focusing region Ra1 of the raw image I1, a reduction in clearness can be avoided.

Although an arithmetic process based on the image information of the point corresponding between two raw images is performed here, a similar process may be performed among three or more raw images. However, between raw images having largely different focus positions during imaging, a point in a focusing region in one raw image may be largely deviated from a focusing region in the other raw image. If the image information of the raw image in an out-of-focus state as just described is included in calculation, the clearness of the image may be largely reduced. Accordingly, only the image information of several raw images having relatively less different focus positions may be used for calculation. For example, raw images whose focus positions are less distant from the point P by a predetermined value or a predetermined number of raw images selected in an increasing order of a distance between the point P and the focus position correspond to raw images used in such a case.

According to the finding of the inventors of this application, the following calculation methods can be, for example, used as a calculation method between raw images effective in reducing speckle noise. Here, V denotes the pixel value representing the point P in the synthesized tomographic image Ia desired to be obtained. V1 denotes the pixel value represented by the image information of the point P1 in the raw image I1 corresponding to the point P. V2 denotes the pixel value represented by the image information of the point P2 in the raw image I2 corresponding the point P. Here, it is assumed that the larger the pixel values V, V1 and V2, the higher the luminance indicated thereby.

A first calculation method is a method for taking a minimum value of the pixel values of the points corresponding to the same position between the respective raw images. Specifically, the pixel value V in the above example is the smaller one of the pixel values V1 and V2. In a tomographic image obtained by imaging cells, spheroids or the like in a liquid, regions of a high luminance corresponding to the cells or the like appear in a background of a low luminance corresponding to the liquid. Speckle noise that changes the luminance of each point into a luminance different from the original one particularly stands out in such an image when bright spots of a high luminance appears in a region of a low luminance. By performing a process of selecting the minimum value of the pixels corresponding to the same position between a plurality of raw images, such noise that tends to stand out can be effectively reduced.

A second calculation method is a method for taking an average value of the pixel values of the points corresponding to the same position between the respective raw images. An image due to the structure of an imaging object is thought to appear in the same manner in each of the plurality of raw images. In contrast, a random luminance variation appearing due to speckle noise differs in each raw image. Thus, by averaging the pixel values of the positions corresponding to each other in the plurality of raw images, the influence of noise can be reduced while keeping an image representing the structure of the imaging object. In this case, a higher noise removal effect is obtained as the number of the raw images used for calculation increases.

A third calculation method is a method for taking a weighted average according to a distance, instead of simply averaging the pixel values of the points corresponding to the same position, between the respective raw images between the point and the focus position. In the second calculation method described above, a speckle noise reducing effect can be improved by calculating the image information of many raw images, but a problem that the clearness of the image is reduced if the image information of the raw image having the focus position largely distant from this position is added remains. Accordingly, if weighted averaging is performed by giving a large weight to the image information for the raw image having the focus position relatively close to this position and giving a smaller weight to the raw image having the more distant focus position, the noise reducing effect and the clearness of the image can be combined.

In the above description, the magnitude of the difference between the pixel values V1 and V2 is not considered to describe the principle of each calculation method. However, it is thought that if the difference between the both is small, the influence of noise is small and an improvement effect by calculation is also small. From this, the pixel value V2 of the point P2 in the focusing region may be directly set as the pixel value V of the point P to maintain the clearness of the image. Specifically, this can be realized by a process of setting the pixel value V2 as the pixel value V without depending on the above calculation if an absolute value of the difference between the pixel values V1 and V2 is smaller than a predetermined threshold value.

Further, a plurality of calculation methods may be implemented in the apparatus and a function of enabling a user to select the calculation method according to how noise appears, a purpose or the like may be provided. For example, tomographic images synthesized by different calculation methods may be displayed on the display section 352 and the calculation method may be selected upon receiving the selection input of the user via the input device 351.

Figure 9A:
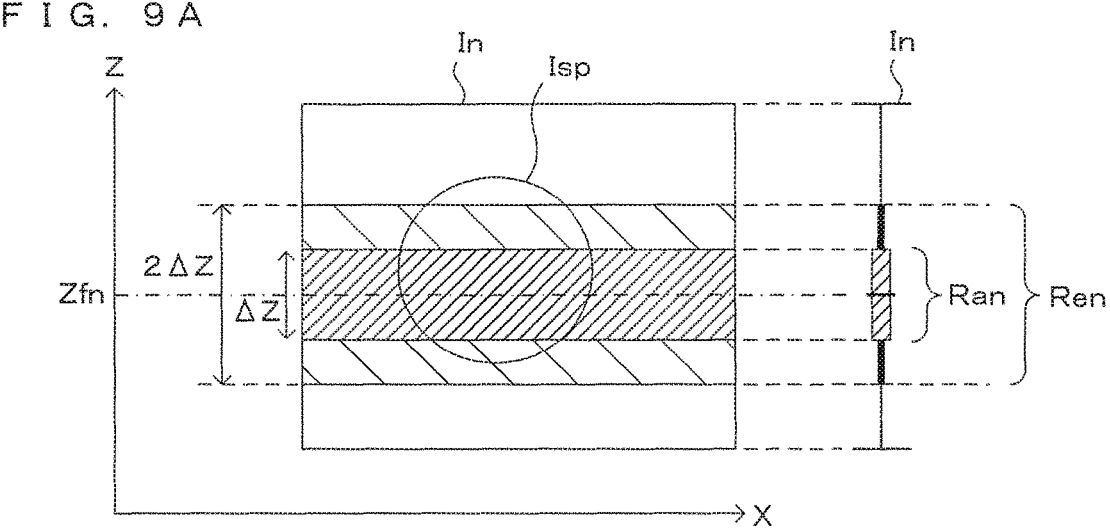
FIGS. 9A and 9B are diagrams showing the allocation of raw images in this embodiment.
Figure 9B:
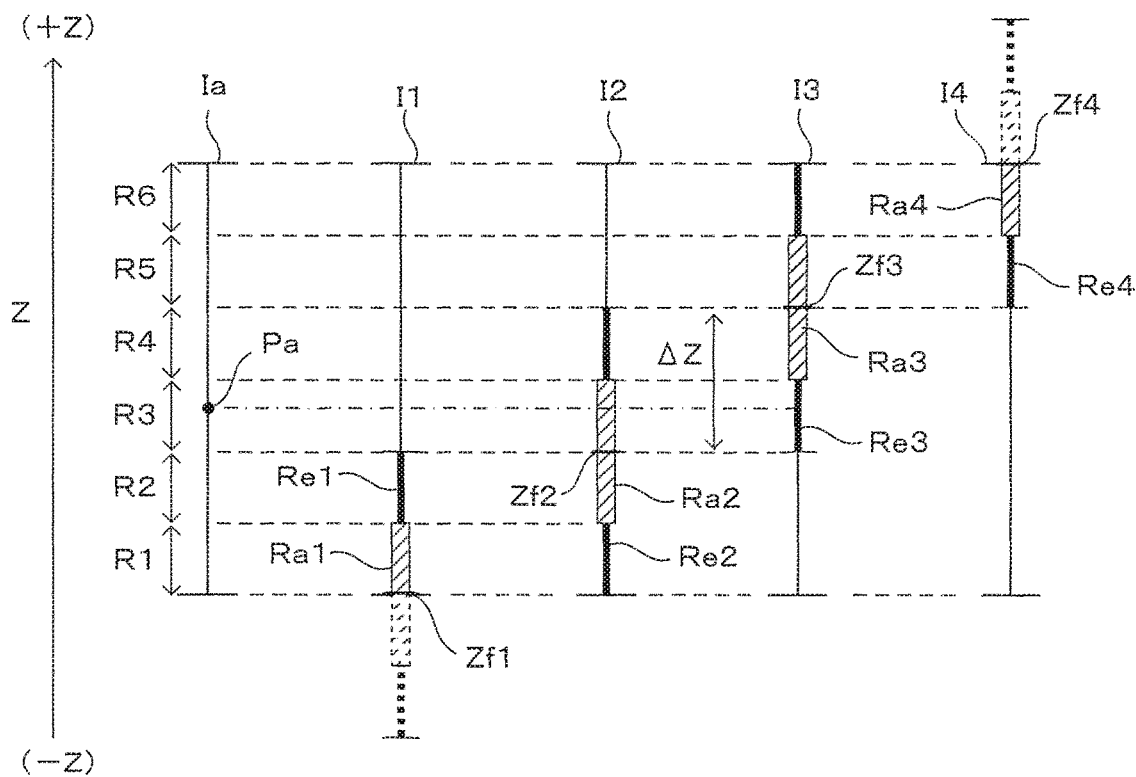

FIGS. 9A and 9B are diagrams showing the allocation of raw images in this embodiment. First, the term of each part is defined as shown in FIG. 9A for one raw image In (n=1, 2, . . . ). Zfn denotes a focal depth (focus position in the Z direction) of the objective lens 23 when the raw image In was imaged. Ran denotes a focusing region included in a depth of field with the focus position Zfn as a center, and ΔZ denotes a length of that focusing region in the Z direction. Inside the focusing region Ran, a clear tomographic image in a focused state is obtained. The extent ΔZ of the focusing region is a value determined by the depth of field of the objective lens 23 and does not depend on the focus position. Thus, the value ΔZ is constant for a plurality of raw images having different focus positions. Therefore, a suffix n is not attached.

Here, a range of an extent 2ΔZ with the focal depth Zfn as a center is defined as an effective region Ren of the raw image In. Inside the effective region Ren with a limited distance from the focal depth Zfn, image quality of a certain level or higher is expected. Specifically, in an area corresponding to the focusing region Ran out of the effective region Ren, a clear image in the focused state is obtained. In an area of the effective region Ren outside the focusing region Ran, image quality is poorer than in the focusing region Ran, but better than in an area more distant from the focus position.

The focal depth Zfn, the positions and extents of the focusing region Ran and the effective region Ren are uniform in the X direction. Therefore, the raw image In is expressed by a linear scale as shown on a right side of FIG. 9A.

FIG. 9B is a diagram showing the allocation of the raw images for generating the tomographic image Ia by synthesis using the above scale. In this embodiment, the raw images are allocated to satisfy the following prerequisites. Note that conditions (B), (C) and (D) ae not independent of each other. Conditions (B), (C) are specified as imaging conditions for realizing the calculation of the condition (D).

(A) The tomographic image Ia to be generated is synthesized from four raw images I1 to I4.

(B) The respective raw images I1 to I4 are so imaged that the focusing regions do not overlap.

(C) An arbitrary point Pa in the tomographic image Ia is included respectively in the focusing region of any one of the raw images and in the effective region outside the focusing region of any one of the other raw images.

(D) A pixel value of the point Pa is obtained based on a pixel value of this point in one raw image including this point in the focusing region and a pixel value of this point in at least one raw image including this point in the effective region (pixel values outside the effective regions are not used).

As shown in FIG. 9B, the tomographic image Ia is generated by successively splicing the following regions along the Z direction from the (−Z) side toward the (+Z) side.

(1) A region R1 for which a pixel value is determined from the focusing region Ra1 of the raw image I1 and the effective region Re2 of the raw image I2.

(2) A region R2 for which a pixel value is determined from the focusing region Ra2 of the raw image I2 and the effective region Re of the raw image I1.

(3) A region R3 for which a pixel value is determined from the focusing region Ra2 of the raw image I2 and the effective region Re3 of the raw image I3.

(4) A region R4 for which a pixel value is determined from the focusing region Ra3 of the raw image I3 and the effective region Re2 of the raw image I2.

(5) A region R5 for which a pixel value is determined from the focusing region Ra3 of the raw image I3 and the effective region Re4 of the raw image I4.

(6) A region R6 for which a pixel value is determined from the focusing region Ra4 of the raw image I4 and the effective region Re3 of the raw image I3.

To enable this, the change amount of the focus position for imaging each time is set at the distance ΔZ corresponding to the depth of field of the objective lens 23 in this embodiment. A size in the Z direction of the tomographic image Ia is determined by a distance between the focus position Zf1 of the raw image I1 having the focus position farthest on the (−Z) side and the focus position Zf4 of the raw image I4 having the focus position farthest on the (+Z) side. Thus, to obtain a tomographic image Ia of a larger size, it is necessary to increase the number of raw images. Further, an imaging range in the Z direction of each raw image is desirably wider than the extent in the Z direction of the tomographic image Ia to be synthesized.

Note that these restriction conditions arise from above prerequisites and the definition that "twice the range ΔZ of the focusing region is the effective region". If the set conditions change, a necessary number of raw images and the change amount of the focus position for imaging each time differ from those described above. For example, in the case of overlapping the focusing regions between the raw images as shown in FIG. 7B, the change amount of the focus position for imaging each time is smaller and, therefore, the necessary number of the raw images increases. Conversely, in the case of providing a gap between the focusing regions of the raw images as shown in FIG. 7C, the necessary number of the raw images can be reduced by increasing the change amount of the focus position. These can be appropriately set according to a level of required image quality and an allowed processing time.

According to the method for generating the tomographic image Ia including the calculation as described above, a pixel value of a pixel at a position of a point in the tomographic image Ia is determined from a pixel value of a point included in the focusing region in one raw image and a pixel value of a point at the same position of the raw image including this point in the effective region. By using the pixel values extracted from the raw images imaged in the focused state or in a state close to the focused state, a reduction in the clearness of the image due to the use of the information on the pixels distant from the focus position can be suppressed. Since how speckle noise appears differs among the raw images imaged at different focus positions, the influence of speckle noise in the synthesized image Ia can be reduced by calculation using the raw image data extracted from the different raw images and corresponding to the same point.

By performing such a process, the focusing range and the range near the focusing range of each of a plurality of raw images having different focusing ranges in the depth direction are extracted and spliced as a result. In this way, clearness similar to that of an all-in-focus image entirely imaged in a state close to the focused state in the depth direction can be obtained. As just described, in this embodiment, a range wide in the depth direction (Z direction) can be imaged even if an optical system having a shallow depth of field is used. Thus, a resolution in the horizontal direction (X direction) can be improved by using an optical system having a large NA. As a result, the image processing apparatus 1 of this embodiment can obtain a good tomographic image having a high resolution in the horizontal direction and the depth direction and good image quality.

Figure 10A:
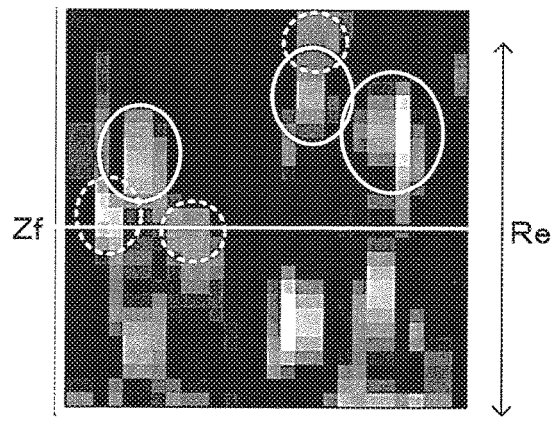
FIGS. 10A to 10C are pictures showing examples of an image obtained in the image processing apparatus of this embodiment.
Figure 10B:
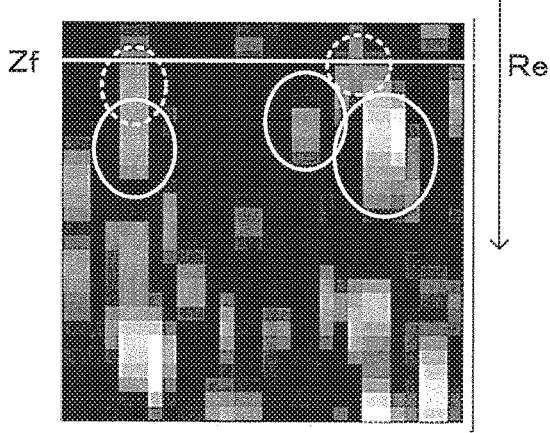
Figure 10C:
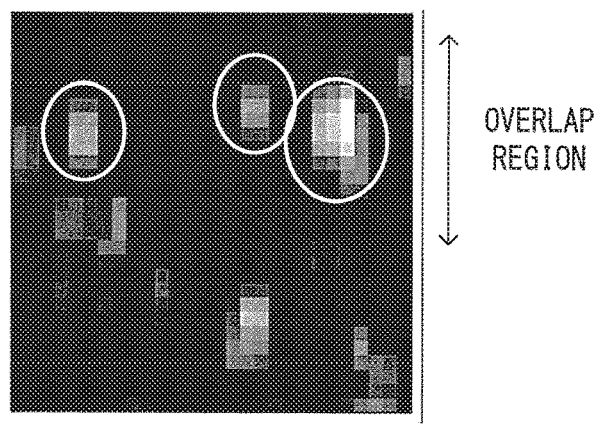

FIGS. 10A to 10C are pictures showing examples of an image obtained in the image processing apparatus of this embodiment. FIGS. 10A and 10B show examples of two raw images obtained by imaging the same position of an imaging object at different focus positions Zf. Further, FIG. 10C shows an example of a tomographic image synthesized from those raw images. The images are largely enlarged and the structure of the imaging object does not clearly appear in order to make bright spots caused by speckle noise having a smaller size than the structure of cells clear.

When FIGS. 10A and 10B are compared in the respective effective regions Re, images enclosed by solid-line circles appear substantially at the same positions in the both images and are estimated to result from the structure of the imaging object. On the other hand, there is a case where images having a low correlation between the both images appear such as parts enclosed by broken-line circles, and these images are estimated to be bright spots appearing due to speckle noise.

FIG. 10C shows an example of a result of synthesizing these raw images and a process of selecting a minimum value of the pixel values at the same position extracted from the two raw images is employed as a calculation process. In an overlap region where the effective regions Re of the two raw images overlap each other, the images commonly appearing in the two raw images are maintained substantially as they are, whereas the luminances of the images having no correlation are largely attenuated. From this, it is found that the influence of speckle noise is reduced by the synthesizing process.

Note that, as shown in FIG. 2A, the imaging unit 20 of the above embodiment is for mixing the signal light L4 and the reference light L5 to cause interference using the beam splitter 22. On the other hand, some of OCT imaging apparatuses are known to cause interference using, for example, an optical fiber coupler besides such a beam splitter as one of various optical devices capable of branching and mixing light waves. As described next, speckle noise can be reduced by providing the above-mentioned processing in the thus configured apparatus as in this embodiment.

Figure 11A:
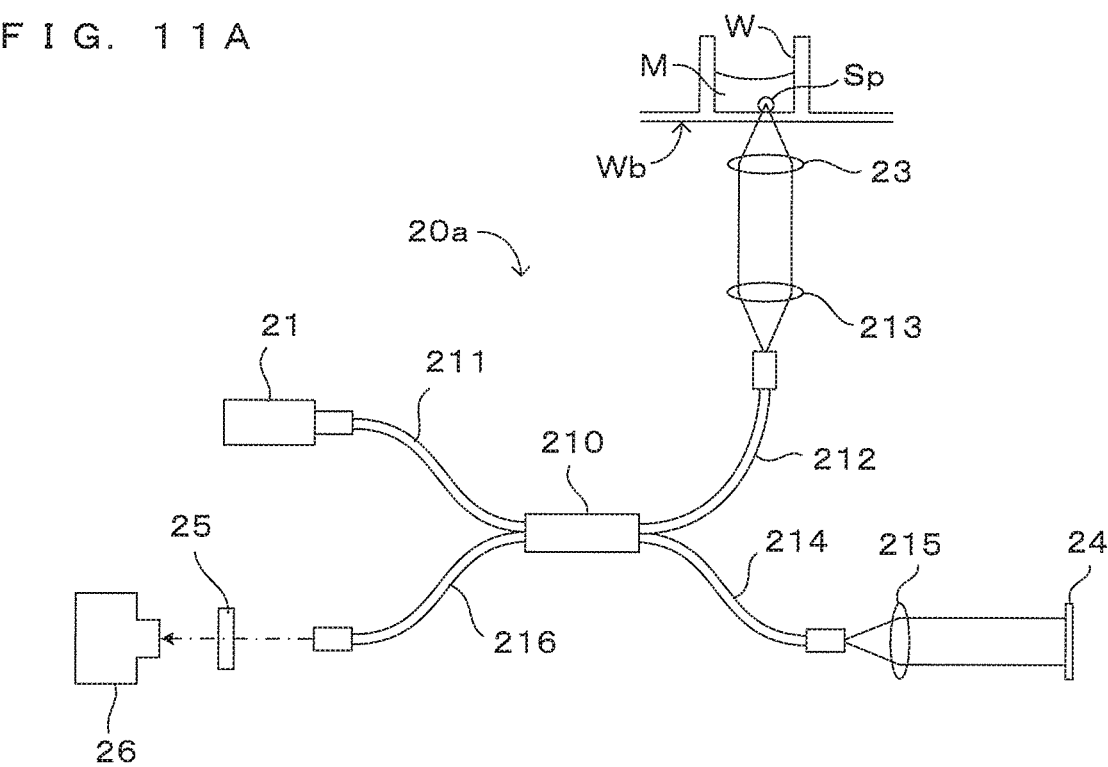
FIGS. 11A and 11B are diagrams showing other configuration examples of the OCT apparatus.
Figure 11B:
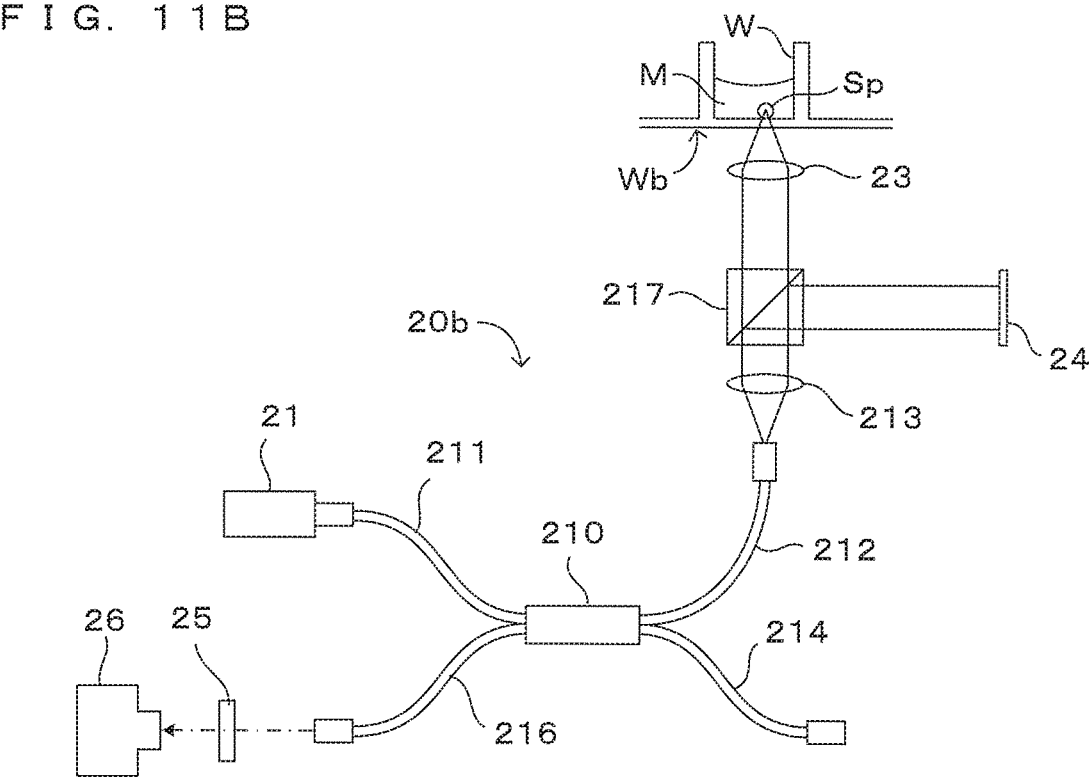

FIGS. 11A and 11B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted.

In an example shown in FIG. 11A, an imaging unit 20a includes an optical fiber coupler 210 instead of the beam splitter 22 as an optical device. An OCT imaging principle for detecting interference light by the optical fiber coupler is not described in detail since it is known.

One optical fiber 211 constituting the optical fiber coupler 210 is connected to a light source 21 and low-coherence light emitted from the light source 21 is branched into lights to two optical fibers 212, 214 by the optical fiber coupler 210. The optical fiber 212 constitutes an object side optical path. More specifically, light emitted from an end part of the optical fiber 212 is incident on an object optical system 200 via a collimator lens 213. Reflected light (signal light) from an imaging object is incident on the optical fiber 212 via the objective lens 23 and the collimator lens 213.

Another optical fiber 214 constitutes a reference side optical path. More specifically, light emitted from an end part of the optical fiber 214 is incident on a reference mirror 24 via a collimator lens 215. Reflected light (reference light) from the reference mirror 24 is incident on the optical fiber 214 via the collimator lens 215. The signal light propagating in the optical fiber 212 and the reference light propagating in the optical fiber 214 interfere in the optical fiber coupler 210 and interference light is incident on a photo-detector 26 via an optical fiber 216 and a spectroscope 25. An intensity distribution of the reflected light on the imaging object is obtained from the interference light received from the photo-detector 26 as in the above embodiment.

Also in an example shown in FIG. 11B, an optical fiber coupler 210 is provided in an imaging unit 20b. However, an optical fiber 214 is not used and a collimator lens 213 and a beam splitter 217 as an optical device are provided on an optical path of light emitted from an optical fiber 212. As in the embodiment described above, an objective lens 23 and a reference mirror 24 are arranged on two optical paths branched by the beam splitter 217. In such a configuration, signal light and reference light are mixed by the beam splitter 217 and interference light generated thereby is guided to a photo-detector 26 through the optical fibers 212, 216.

Also by those configurations, it is possible to generate a tomographic image similar to that of the above embodiment by performing imaging every time the objective lens 23 is moved in the Z direction and the focus position thereof is changed. Since collimated light is incident on the objective lens 23, a position change amount of the objective lens 23 directly serves as the change amount of the focus position.

As described above, in the image processing apparatus 1 of this embodiment, the imaging unit 20 functions as a "data acquisitor" of the invention, and the light source 21, the beam splitter 22, the objective lens 23, the reference mirror 24, the spectroscope 25, the photo-detector 26 and the like thereof integrally constitute an "imager" of the invention. Further, the focusing mechanism 29 functions as a "focusing unit" of the invention. Further, the CPU 31, the signal processor 33 and the like of the control unit 30 function as an "image generator" of the invention.

Further, in the above embodiment, Steps S102 to S107 of FIG. 5 correspond to a "data acquisition step" of the invention, whereas Steps S108 to S110 corresponds to an "image generation step" of the invention. Further, in the above embodiment, the raw image data representing each of the raw images I1 to I4 obtained by the Fourier transform of the spectra of the interference signals correspond to "imaging data" of the invention.

Note that the invention is not limited to the above embodiment and various changes other than those described above can be made without departing from the gist of the invention. For example, the above embodiment is a so-called Fourier domain OCT imaging apparatus for obtaining a reflected light intensity distribution in a depth direction from intensity of interference at each wavelength using illumination light including wavelength components in a wide range. However, besides this, the invention can be applied to various imaging apparatuses for tomographic imaging using the OCT imaging principle such as a time domain OCT imaging apparatus.

A time domain OCT imaging apparatus has a function of changing an optical path length of reflected light by moving a reference mirror and images an imaging object by scanning the imaging object in a depth direction by a movement of the reflection mirror. Thus, the position of a reference surface with respect to the imaging object can be linked with a focus position in imaging a raw image by changing a focal depth. Utilizing this, it is, for example, possible to perform imaging by scanning only a range near the focus position in the depth direction. This enables the imaging of a part not used in a final tomographic image to be omitted. However, alignment taking into account a change of the reference surface is necessary in synthesizing the raw images.

Further, in the above embodiment, the raw image data of the raw images obtained by the Fourier transform of the spectra of the interference signals is used as the "imaging data" of the invention and the pixel value of each pixel of the tomographic image to be synthesized is determined based on the raw image data. Instead of this, the raw images can be synthesized using spectrum data before the Fourier transform. Specifically, a wavelength axis of a spectrum obtained by FD-OCT imaging represents a position in the depth direction. Thus, it is possible to specify to which position of an imaging object one wavelength in the spectrum corresponds. Further, which position in each spectrum corresponds to the focus position can be also known.

Accordingly, intensities of signal lights corresponding to the same position of the imaging object can be compared between spectra obtained by imaging a plurality of times. The "synthesized" spectrum can be obtained by calculation between those. By the Fourier transform of the thus obtained spectrum, the targeted tomographic image can be generated. In this case, the spectrum data corresponds to the "imaging data" of the invention.

Further, in the calculation method of the above embodiment, the pixel value of each pixel of the tomographic image is determined from the raw image data of the focusing region of one raw image and the effective region of another raw image. However, this is an example of the calculation method. As described above, how the focusing regions overlap, from how many raw images the tomographic image is to be generated, which calculation method is employed and the like are arbitrary.

Further, in the image processing apparatus 1 described above, the imaging unit 20 having a function as the "data acquisitor" of the invention has an imaging function. However, the invention can be realized as an image processing apparatus having no imaging function. Specifically, the invention can be embodied as an image processing apparatus for receiving image data generated by an imaging apparatus for performing imaging similar to that described above and performing calculation using this image data. In this case, an interface for receiving the image data functions as the "data acquisitor" of the invention. Further, an apparatus in charge of an imaging function and an apparatus in charge of an image processing function may be separately configured. In this case, these apparatuses integrally function as the "image processing apparatus" of the invention.

Further, the "image generator" of the invention can be also realized by causing a computer device having a general hardware configuration to implement a control program for performing the above calculation. Specifically, the image processing apparatus 1 may be configured by combining an imaging apparatus having the imaging unit 20, the drive controller 40 and a minimum control function of causing these to operate and a personal computer or the like functioning as the control unit 30 by implementing a control program describing the above processing contents. Thus, the invention can be provided to users in the form of such a control program.

As the specific embodiment has been illustrated and described above, in this invention, the value of the pixel may increase with an increase in luminance and the image generator may set the value of the pixel at a minimum value of the image data corresponding to the pixel obtained by the plurality of imaging. According to such a configuration, bright spots due to speckle noise, which particularly causes an image quality reduction in the imaging of cells or the like, can be removed.

Further, the image generator may also set the value of the pixel at an average value of the image data corresponding to the pixel obtained by the plurality of imaging. According to such a configuration, it is possible to reduce speckle noise appearing in a non-correlated manner in imaging a plurality of times while maintaining an image of an imaging object appearing in images in the same manner even if a focus position is changed.

Further, the image generator may set the value of the pixel at a weighted average value of the image data corresponding to the pixel obtained by each of the plurality of imaging according to a distance from the pixel to a focus position during imaging. According to such a configuration, reductions in the clearness and contrast of the image associated with noise removal can be suppressed by giving different weights to pixels close to the focus position and clearly showing the imaging object and unclear pixels distant from the focus position.

Further, the data acquisitor of the invention may the data acquisitor includes: an imager which has an objective lens and images the imaging object by an optical coherence tomographic imaging, an objective lens having an optical axis parallel to the depth direction and converging illumination light on the imaging object; and a focusing unit which changes a focus position of the objective lens in the depth direction. According to such a configuration, imaging data necessary to generate a synthesized tomographic image can be obtained by the focusing unit changing and setting the focus position of the objective lens and the imager performing imaging at each focus position.

Further, in the image processing method of the invention, a multitude of focus positions may set such that each position in a cross-section is imaged in a focused state at least by imaging one time and imaging is performed at each of the focus positions in the data acquisition. According to such a configuration, calculation can be performed using image data obtained in the focused state at each pixel constituting a tomographic image. Thus, the quality of the tomographic image can be improved.

This invention can be applied to OCT imaging techniques in general. Particularly, this invention can be suitably applied in the fields of medicine, biochemistry and drug discovery for imaging cells and cell clusters cultured in a container such as a well plate.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An image processing apparatus for generating, by optical coherence tomographic imaging, a tomographic image corresponding to one cross-section of an object, the image processing apparatus comprising:
   a data acquisitor that images the one cross-section of the object a plurality of times at mutually different focus positions along a depth direction parallel with an incident direction of illumination light in order to acquire images of the one cross-section of the object, the images having imaging ranges different from each other according to the mutually different focus positions of the images, the imaging ranges of the images being shifted in the depth direction and each imaging range overlapping at least adjacent one of the imaging ranges; and an image generator which synthesizes the images to generate the tomographic image corresponding to the cross-section parallel to the depth direction, the image generator setting values of pixels of the tomographic image based on values of respectively corresponding pixels of the images, wherein one pixel in the tomographic image corresponds to at least (1) a first point in a first image of the images and (2) a second point in a second image of the images, the first point and the second point corresponding to a same point in an overlapped range of imaging ranges of the first and second images, the image generator calculates a value of the one pixel in the tomographic image based on a first value of a pixel corresponding to the first point in the first image and a second value of a pixel corresponding to the second point in the second image, and the image generator sets the value of the one pixel to one of the first and second values which is smaller than another.

2. The image processing apparatus of claim 1, wherein the data acquisitor includes:

an imager which has an objective lens and images the object by the optical coherence tomographic imaging, an objective lens having an optical axis parallel to the depth direction and converging the illumination light on the object; and a focusing unit which changes a focus position of the objective lens in the depth direction.

3. The image processing apparatus of claim 1, wherein the one pixel in the tomographic image corresponds to (3) a third point in a third image of the images in addition to the first and second points, the third point corresponding to the same point in the overlapped range of the imaging ranges of the first to third images, and the image generator calculates the value of the one pixel in the tomographic image based on the first value of the pixel corresponding to the first point in the first image, the second value of the pixel corresponding to the second point in the second image, and a third value of a pixel corresponding to the third point in the third image.

4. An image processing apparatus for generating, by optical coherence tomographic imaging, a tomographic image corresponding to one cross-section of an object, the image processing apparatus comprising:

a data acquisitor that images the one cross-section of the object a plurality of times at mutually different focus positions along a depth direction parallel with an incident direction of illumination light in order to acquire images of the one cross-section of the object, the images having imaging ranges different from each other according to the mutually different focus positions of the images, the imaging ranges of the images being shifted in the depth direction and each imaging range overlapping at least adjacent one of the imaging ranges; and an image generator which synthesizes the images to generate the tomographic image corresponding to the cross-section parallel to the depth direction, the image generator setting values of pixels of the tomographic image based on values of respectively corresponding pixels of the images, wherein one pixel in the tomographic image corresponds to at least (1) a first point in a first image of the images and (2) a second point in a second image of the images, the first point and the second point corresponding to a same point in an overlapped range of imaging ranges of the first and second images, the image generator calculates a value of the one pixel in the tomographic image based on a first value of a pixel corresponding to the first point in the first image and a second value of a pixel corresponding to the second point in the second image, and the image generator sets the value of the one pixel at a weighted average value of the first and second values according to a distance from the first point of the first image to a corresponding focus position of the first image and a distance from the second point of the second image to a corresponding focus position of the second image.

5. An image processing method for generating, by optical coherence tomographic imaging, a tomographic image corresponding to one cross-section of an object, the image processing method comprising:

imaging the one cross-section of the object a plurality of times at mutually different focus positions along a depth direction parallel with an incident direction of illumination light in order to acquire images of the one cross-section of the object, the images having imaging ranges different from each other according to the mutually different focus positions of the images, the imaging ranges of the images being shifted in the depth direction and each imaging range overlapping at least adjacent one of the imaging ranges; and synthesizing the images to generate the tomographic image corresponding to the cross-section parallel to the depth direction, the synthesizing step including setting values of pixels of the tomographic image based on values of respectively corresponding pixels of the images, wherein one pixel in the tomographic image corresponds to at least (1) a first point in a first image of the images and (2) a second point in a second image of the images, the first point and the second point corresponding to a same point in an overlapped range of imaging ranges of the first and second images, the synthesizing steps incudes calculating a value of the one pixel in the tomographic image based on a first value of a pixel corresponding to the first point in the first image and a second value of a pixel corresponding to the second point in the second image, and the imaging step includes setting the value of the one pixel to one of the first and second values which is smaller than another.

6. The image processing method of claim 5, wherein the imaging step includes setting the different focus positions so that one of points in the one cross-section of the object is imaged in a focused state each time the one cross-section of the object is imaged.

7. The image processing method of claim 5, wherein the one pixel in the tomographic image corresponds to (3) a third point in a third image of the images in addition to the first and second points, the third point corresponding to the same point in the overlapped range of the imaging ranges of the first to third images, and the synthesizing steps includes calculating the value of the one pixel in the tomographic image based on the first value of the pixel corresponding to the first point in the first image, the second value of the pixel corresponding to the second point in the second image, and a third value of a pixel corresponding to the third point in the third image.

8. An image processing method for generating, by optical coherence tomographic imaging, a tomographic image corresponding to one cross-section of an object, the image processing method comprising:
  imaging the one cross-section of the object a plurality of times at mutually different focus positions along a depth direction parallel with an incident direction of illumination light in order to acquire images of the one cross-section of the object, the images having imaging ranges different from each other according to the mutually different focus positions of the images, the imaging ranges of the images being shifted in the depth direction and each imaging range overlapping at least adjacent one of the imaging ranges; and
  synthesizing the images to generate the tomographic image corresponding to the cross-section parallel to the depth direction, the synthesizing step including setting values of pixels of the tomographic image based on values of respectively corresponding pixels of the images, wherein
  one pixel in the tomographic image corresponds to at least (1) a first point in a first image of the images and (2) a second point in a second image of the images, the first point and the second point corresponding to a same point in an overlapped range of imaging ranges of the first and second images,
  the synthesizing steps incudes calculating a value of the one pixel in the tomographic image based on a first value of a pixel corresponding to the first point in the first image and a second value of a pixel corresponding to the second point in the second image, and
  the synthesizing step includes setting the value of the pixel at a weighted average value of the first and second values according to a distance from the first point of the first image to a corresponding focus position of the first image and a distance from the second point of the second image to a corresponding focus position of the second image.

* * * * *